（12) United States Patent
Fisher et al.

(10) Patent No.: US 8,481,773 B2
(45) Date of Patent: Jul. 9, 2013

(54) VOLATILE CYCLIC SILOXANES

(75) Inventors: Mark David Fisher, Midland, MI (US);
Michael Kang-Jen Lee, Midland, MI
(US); Bi-Shun Zeng, Midland, MI (US)

(73) Assignee: DOW Corning Corporation, Midland,
MI (US)

( * ) Notice: Subject to any disclaimer, the term of this
patent is extended or adjusted under 35
U.S.C. 154(b) by 0 days.

(21) Appl. No.: 13/511,038

(22) PCT Filed: Nov. 24, 2010

(86) PCT No.: PCT/US2010/057962
§ 371 (c)(1),
(2), (4) Date: May 21, 2012

(87) PCT Pub. No.: WO2011/071698
PCT Pub. Date: Jun. 16, 2011

(65) Prior Publication Data
US 2012/0276026 A1    Nov. 1, 2012

Related U.S. Application Data

(60) Provisional application No. 61/264,283, filed on Nov. 25, 2009.

(51) Int. Cl.
*C07F 7/08*    (2006.01)

(52) U.S. Cl.
USPC ........................................................ 556/406

(58) Field of Classification Search
None
See application file for complete search history.

(56) References Cited

FOREIGN PATENT DOCUMENTS
WO    2008085360    7/2008

OTHER PUBLICATIONS

English translation of Saad, Chemiker Zeitung, 1977.*
English translation of Calas, Comptes Rendus Hebdomadaires Des Seances De L'Academie Des Sciences, 1959.*
Nguyen, V.Q. et al.: "Franck-Condon Dominated Chemistry. Dissociations of Silicon-Centered Radicals Prepared by Femtosecond Reduction of Their Cations in the Gas Phase", Journal of Physical Chemistry, vol. 99, No. 42, Oct. 19, 1995, pp. 15454-15464.
Nedogrei, E.P. et al.: "Reaction of octamethyltrisiloxane with 2-alkoxy-1, 3-dioxacycloalkanes", Jouranl of General Chemistry of the USSR, vol. 60, No. 11, 1990, pp. 2231-2234.
Zhurkina, I.P. et al.: "Reaction of octamethylcyclotetrasiloxane with 2-ethoxy-1,3-dioxanes", Doklady Chemistry, vol. 304, No. 1-6, 1989, pp. 49-50.
Razuvaev, G.Z. et al: "Oxidation of organopolysilanes with pi- and n-donor substituents with peroxybenzoic acid", Journal of General Chemistry of the USSR, vol. 57, No. 2, 1987, pp. 323-330.

(Continued)

*Primary Examiner* — Paul Dickinson
(74) *Attorney, Agent, or Firm* — Alan Zombeck

(57) ABSTRACT

This application relates to cyclic siloxane compounds comprising the structural formula where $a \geq 2$ and $b \geq 2$, R is an alkyl group containing 1 to 4 carbon atoms, R1 is independently hydrogen or methyl, compositions comprising any of the above cyclic siloxanes and an additional silicone, emulsion compositions comprising any of the above cyclic siloxanes or the above composition, and a process for preparing the above cyclic siloxane compounds comprising reacting a chloro end-blocked polydimethylsiloxane with a diol functional compound containing at least 3 carbon atoms.

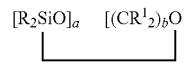

8 Claims, 2 Drawing Sheets

Sensory Test Results for the Cyclic Siloxane of Example 2 Compared to $D_5$

OTHER PUBLICATIONS

Saad, S.M. et al: "Zur Darstellung von 1,1,3,3-Tetramethyl-1,3-disila-2,4,7-triox a-cycloheptan (1) and 1,1,3,3-Tetramethyl-1,3-disila-2,4,8-triox a-cyclooctan (2)-Preparation of 1,1,3,3-Tetramethyl-1, 3-disila-2,4,7-triox a-cyclohept ane and 1,1,3,3-Tetramethyl-1, 3-disila-2,4,8-trio xa-cyclooctane", Chemiker Zeitung, vol. 101, No. 5, 1977, p. 262.

Lebedev, E.P. et al.: Coalcoholysis of organosilazanes and organocyclosilazaoxanes with oragnochlorosilanes and organochlorosiloxanes, Journal of General Chemistry of the USSR, vol. 45, No. 12, 1975, pp. 2606-2610.

Galas, R. et al.: Effets steriques dans la condensation de composes alpha-dihydroxyles avec des derives dichlorosilicoes. Generalisation—Steric effects in the condensation of alph-dihydroxy compounds with dichlorosilane derivatives. Generalisation, Comptes Rendus Hebdomadaires Des Seances De L'Academie Des Sciences, vol. 249, 1959, pp. 1011-1013.

* cited by examiner

Sensory Test Results for the Cyclic Siloxane of Example 2 Compared to $D_5$

Sensory Test Results for the Cyclic Siloxane of Example 3 Compared to $D_5$

VOLATILE CYCLIC SILOXANES

CROSS REFERENCE TO RELATED APPLICATIONS

This application is a U.S. national stage filing under 35 U.S.C. §371 of PCT Application No. PCT/US10/57962 filed on Nov. 24, 2010, currently pending, which claims the benefit of U.S. Provisional Patent Application No. 61/264,283 filed Nov. 25, 2009 under 35 U.S.C. §119 (e). PCT Application No. PCT/US10/57962, U.S. Provisional Patent Application No. 61/264,283 are hereby incorporated by reference.

BACKGROUND OF THE INVENTION

Siloxane monomers, polymers, and elastomers embrace a unique combination of properties such as excellent high temperature and weather stability, extreme low temperature flexibility, high compressibility, high electrical resistivity, low dielectric loss, high gas permeability, odorless, tasteless, non-toxic etc. Because of these unique properties, silicones are widely used in industrial and consumer product applications. Specifically, octamethylcyclotetrasiloxane ($D_4$) and decamethylcyclopentasiloxane ($D_5$) offer some compelling properties to the personal care market place. These cyclosiloxanes along with some other low molecular weight linear siloxanes offer superior wetting properties combined with excellent volatility profile that make them highly attractive in the delivery of a variety of personal care products ranging from antiperspirants to shampoo to skin lotions.

Formulators of personal care products continually seek new compounds for incorporation into consumer products. Thus, a need exists to identify new cyclic siloxanes as alternatives to $D_4$ or $D_5$, yet having similar physical properties.

BRIEF SUMMARY OF THE INVENTION

The present inventors have discovered certain cyclic siloxanes which are chemically differentiated from octamethylcyclotetrasiloxane ($D_4$) and decamethylcyclopentasiloxane ($D_5$), yet having similar physical properties.

The present invention provides cyclic siloxanes compounds having the structural formula

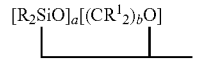

where $a \geq 2$ and $b \geq 2$,

R is an alkyl group containing 1 to 4 carbon atoms, $R^1$ is independently hydrogen or methyl.

This invention further relates to a process for preparing cyclic siloxanes by reacting a chloro end blocked polydimethylsiloxane with a diol functional compound containing at least 2 carbon atoms.

The present cyclic siloxanes have similar physical properties as octamethylcyclotetrasiloxane ($D_4$) and decamethylcyclopentasiloxane ($D_5$). Therefore, they are useful in a variety of personal care compositions.

DETAILED DESCRIPTION OF THE INVENTION

Figure 1:
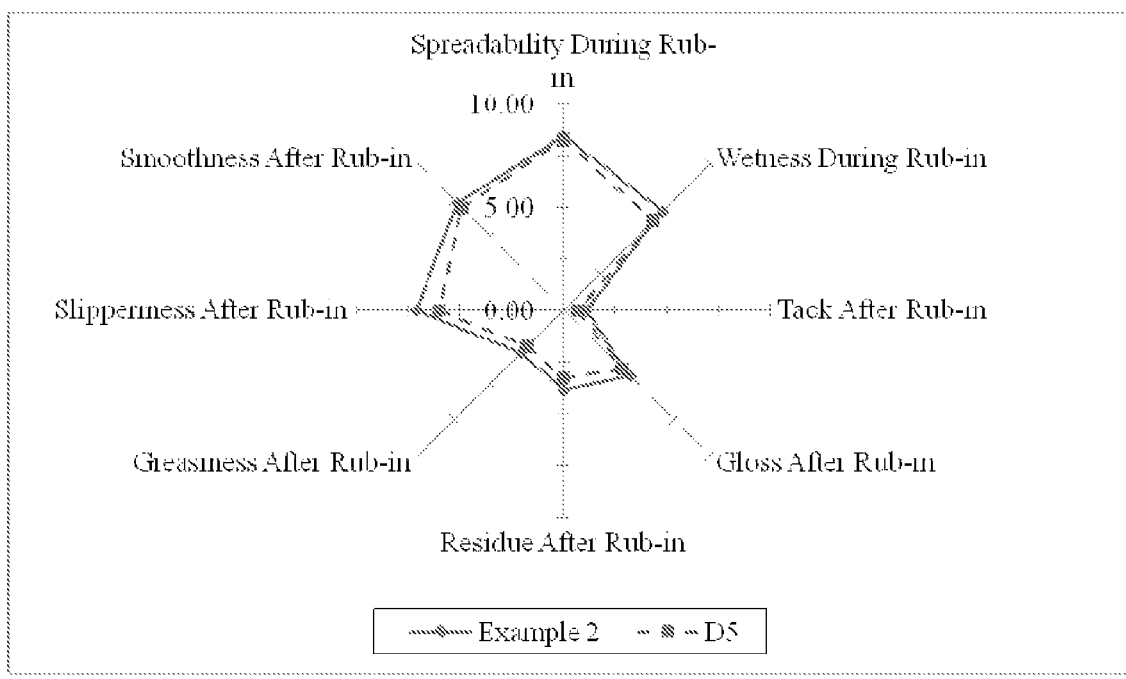
FIG. 1: Sensory Test Results for the Cyclic Siloxane of Example 2 Compared to $D_5$

The present disclosure relates to cyclic siloxane compounds comprising the structural formula

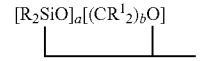

where $a \geq 2$ and $b \geq 2$,
R is an alkyl group containing 1 to 4 carbon atoms, alternatively R is methyl.
$R^1$ is independently hydrogen or methyl.
In the above formula $[R_2SiO]$ represents a dialkylsiloxy unit. There are at least two dialkylsiloxy units in the present cyclic siloxanes, as indicated by the subscript "a" having a value of $\geq 2$, alternatively a may range from 2 to 8, alternatively from 2 to 6, alternatively from 2 to 4, or alternatively 2 to 3.

In the above formula $(CR^1_2)$ represents an alkylene or oxyalkylene group. The alkylene group contains at least two carbon atoms, as indicated by the subscript b. $R^1$ in the formula may be a hydrogen atom or a methyl group. Thus, the $(CR^1_2)_b$ segment may be for example selected from the following alkylene groups; —CH$_2$CH$_2$—, —CH$_2$CH$_2$CH$_2$—, —CH$_2$CH(CH$_3$)CH$_2$—, —CH(CH$_3$)CH$_2$CH$_2$—, —CH$_2$CH$_2$C(CH$_3$)$_2$—, —C(CH$_3$)$_2$CH$_2$C(CH$_3$)$_2$—, —CH$_2$CH$_2$CH$_2$CH$_2$—, —CH$_2$CH$_2$CH$_2$CH(CH$_3$)—, —CH$_2$CH$_2$CH$_2$C(CH$_3$)$_2$—, —CH(CH$_3$)CH$_2$C(CH$_3$)$_2$—, or —C(CH$_3$)$_2$CH$_2$C(CH$_3$)$_2$—. Alternatively, the $(CR^1_2)_b$ segment is —CH(CH$_3$)CH$_2$CH$_2$—, or —CH(CH$_3$)CH$_2$C(CH$_3$)$_2$—, —CH$_2$CH$_2$—O—CH$_2$CH$_2$—, —CH$_2$CH$_2$CH$_2$—O—CH$_2$CH$_2$CH$_2$—.

In one embodiment, the cyclic siloxane is 2,2,4,4,6,6,8-heptamethyl-1,3,5-trioxa-2,4-disilacyclooctane having the formula;

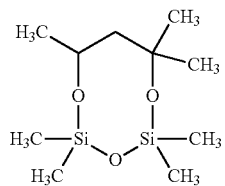

In one embodiment, the cyclic siloxane is 2,2,4,4,6,6,8-heptamethyl-1,3,5,7-tetraoxa-2,4,6-trisilacyclodecane having the formula;

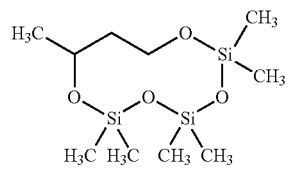

In one embodiment, the cyclic siloxane is 2,2,4,4,6-pentamethyl-1,3,5-trioxa-2,4-disilacyclooctane having the formula;

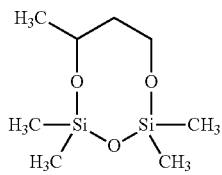

In one embodiment, the cyclic siloxane is 1 2,2,4,4,6-pentamethyl-1,3,5-trioxa-2,4-disilacycloheptane having the formula

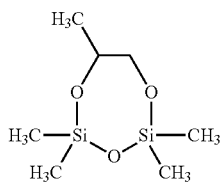

The present cyclic siloxanes may be prepared by various methods. Alternatively, the cyclic siloxanes may be prepared according to the process as described herein.

The present disclosure provides a process for preparing cyclic siloxanes by reacting a chloro end blocked polydialkylsiloxane, alternatively a polydimethylsiloxane, with a diol functional compound containing at least 2 carbon atoms.

Chloro end blocked polydimethylsiloxanes are known and may be represented by the following average formula;

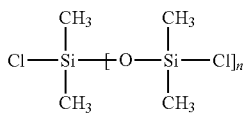

where n is typically 1 or 2. They may be prepared as illustrated below;

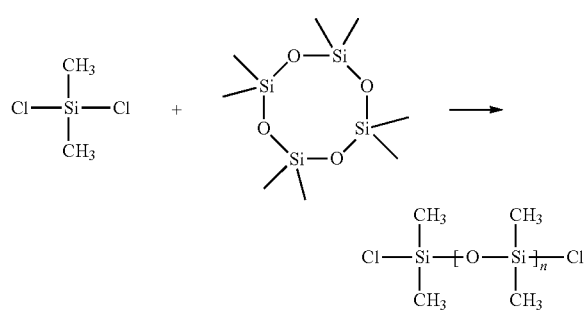

The diol functional compound containing at least two carbon atoms may be selected from those organic compounds containing at least two hydroxy functional groups. Typically, the diol functional compound is a diol functional hydrocarbon containing at least 3 carbon atoms, alternatively at least 4 carbon atoms, alternatively at least 5 carbon atoms, or alternatively at least 6 carbon atoms. Representative, non-limiting examples include; 1,2-propanediol, 1,3-propanediol 1,3-butanediol,hexylene glycol, 1,2-butanediol, 1,4-butanediol, 2,3-butanediol, 1,2-pentanediol, 1,4-pentanediol, 1,5-pentanediol, 2,4-pentanediol, 1,2-hexanediol, 1,5-hexanediol, 1,6-hexanediol, 2,5-hexanediol, 1,3-cyclohexanediol, 3-methyl-1,5-pentanediol, 2,6-heptanediol, 1,2-cyclopentanediol, 2-methyl-2,3-butanediol, diethylene glycol, dipropylene glycol, 1,2 hexanediol, 3,3-dimethyl-1,2-butanediol, 4-methyl-2,3-pentanediol, 2,4-dimethyl-2,4-pentanediol, cyclopentane-1,3-diyldimethanol, 3-fluoro-1,2-propanediol.

The reaction between the chloro endblocked polydimethylsiloxane and the diol functional compound may be neat or in a solvent. Typically, the reaction is conducted in a solvent, where the solvent is selected from an aprotic polar organic solvent. Exemplary aprotic organic solvents include low molecular weight organic esters such as methyl acetate, ethyl acetate, ethyl propionate, isopropyl acetate, propyl acetate, ethyl fluoroacetate, butyl acetate, propyl propionate, ethyl butyrate, isobutyl acetate, ethyl isobutyrate, sec-butyl acetate, and other solvents such as tetrahydrofuran, acetone, methylisobutyl ketone, 2-methyltetrahydrofuran, 2,5-dimethyltetrahydrofuran, 2-butoxyethyl acetate.

The reaction between the chloro endblocked polydimethylsiloxane and the diol functional compound is typically enhanced by the addition of an organic amine compound. The added amine reacts with hydrogen chloride ion formed in the reaction to form an amine salt, which may be filtered or easily separated from the cyclic siloxane product. Exemplary amines include; hexyl amine, pyridine, diethylamine, diethylmethylamine, ethylisopropylamine, dipropylamine, ethylbutylamine, diisopropylamine, dibutylamine, trimethylamine, triethylamine, N,N-dimethylbutylamine, n-methyldipropylamine, tripropylamine, tributylamine, triisobutylamine, tripentylamine, n,n-dibutyl-n-methylamine, 1-methylpyrrolidine, 1-butylpyrrolidine, 2-methylpyridine, 3-methylpyridine, 4-methylpyridine, pyrrolidone, 2-methylpyrrolidine, 2,5-dimethylpyrrolidine.

The order of addition in the reaction may vary, but typically the chloro endblocked polydimethylsiloxane and diol functional compound are added simultaneously to the reaction solvent medium. Typically, the rates of each are adjusted to be approximately the same, and both are added at such a rate so as the addition was completed in about 1 hour.

The reaction is conducted at a temperature of 0 to 200° C., alternatively from 30 to 120° C., or alternatively from 50 to 80° C., at atmospheric conditions.

The amounts of the chloro endblocked polydimethylsiloxane and diol functional compound used in the reaction may vary, but typically the reaction is conducted at approximately a 1:1 mole ratio of each reactant. Alternatively, the reaction is conducted with a slight excess, such as a 10% molar excess, of the diol compound, to ensure complete consumption of the chloro endblocked polydimethylsiloxane.

The cyclic siloxane may be isolated and/or purified by using common distillation techniques.

Alternatively, instead of using chloro endblocked polydimethylsiloxane to react with the diol functional compound, the chloro group may be replaced with other groups that react in a condensation reaction. Such groups include acetoxy, oxime, silanol, and silazane groups.

Alternatively, the cyclic siloxanes of the present disclosure may be prepared by a condensation reaction, as illustrated below.

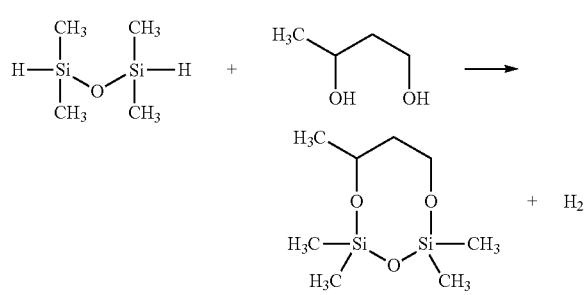

The cyclic siloxanes may be combined with other silicone compositions. For example, such silicones include; silicone fluids, gums, resins, elastomers, silicone surfactants and emulsifiers such as silicone polyethers, organofunctional silicones such as aminofunctional silicones and alkylmethylsiloxanes.

Alkylmethylsiloxanes may be combined with the present cyclic siloxanes. The alkylmethylsiloxanes siloxane polymers generally will have the formula $Me_3SiO[Me_2SiO]_y$ $[MeRSiO]_zSiMe_3$, in which R is a hydrocarbon group containing 6-30 carbon atoms, Me represents methyl, and the degree of polymerization (DP), i.e., the sum of y and z is 3-50. Both the volatile and liquid species of alkymethysiloxanes can be used in the composition.

Silicone gums may be combined with the present cyclic siloxanes. As used herein, silicone gums refer to polydiorganosiloxane gums. Silicone gums are known in the art and are available commercially. They consist of generally insoluble polydiorganosiloxanes having a viscosity in excess of 1,000,000 centistoke ($mm^2/s$) at 25° C., alternatively greater than 5,000,000 centistoke ($mm^2/s$) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke ($mm^2/s$) at 25° C., to 20 million centistoke ($mm^2/s$) at 25° C.

Silicone resins may be combined with the present cyclic siloxanes. These resin compositions are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Water soluble or water dispersible silicone polyether compositions may be included in compositions containing the present cyclic siloxanes. Silicone polyethers are also known as polyalkylene oxide silicone copolymers, silicone poly (oxyalkylene) copolymers, silicone glycol copolymers, or silicone surfactants. These can be linear rake or graft type materials, or ABA type where the B is the siloxane polymer block, and the A is the poly(oxyalkylene) group. The poly (oxyalkylene) group can consist of polyethylene oxide, polypropylene oxide, or mixed polyethylene oxide/polypropylene oxide groups. Other oxides, such as butylene oxide or phenylene oxide are also possible.

The present cyclic siloxanes may be incorporated into the oil phase of o/w, w/o, w/s, or multiple phase emulsions using organic or silicone emulsifiers. As used herein, "emulsifier" refers to any compound or substance that enables the formation of an emulsion. The emulsifier may be selected from any ionic, nonionic, or zwitterionic surfactant capable of stabilizing emulsions. The surfactant may be an anionic surfactant, cationic surfactant, nonionic surfactant, amphoteric surfactant, or a mixture of surfactants.

Representative examples of suitable anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates. One example of a preferred anionic surfactant is sold commercially under the name Bio-Soft N-300. It is a triethanolamine linear alkylate sulphonate composition marketed by the Stephan Company, Northfield, Ill.

Representative examples of suitable cationic surfactants include alkylamine salts, quaternary ammonium salts, sulphonium salts, and phosphonium salts. Representative examples of suitable nonionic surfactants include condensates of ethylene oxide with long chain fatty alcohols or fatty acids such as a $C_{12-16}$ alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, and fatty amine oxides. Representative examples of suitable amphoteric surfactants include imidazoline compounds, alkylaminoacid salts, and betaines.

Representative examples of suitable commercially available nonionic surfactants include polyoxyethylene fatty alcohols sold under the tradename BRIJ by Uniqema (ICI Surfactants), Wilmington, Del. Some examples are BRIJ 35 Liquid, an ethoxylated alcohol known as polyoxyethylene (23) lauryl ether, and BRIJ 30, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S-40. When mixtures containing nonionic surfactants are used, one nonionic surfactant should have a low Hydrophile-Lipophile Balance (HLB) and the other nonionic surfactant should have a high HLB, such that the two nonionic surfactants have a combined HLB of 11-15, alternatively a combined HLB of 12.5-14.5.

The emulsifier may also be chosen to from a water/oil or a water/silicone emulsifier, such as silicone polyether emulsifiers. Silicone polyethers (SPEs) generally refer to silicones containing polyether or polyoxyalkylene groups, which could take in many different structural forms. Typically such forms are either rake-type or ABA type SPEs which are derived most commonly from hydrosilylation of SiH functional organosiloxanes with allyloxy-functional polyethers in the presence of a Pt catalyst The silicone polyethers disclosed in U.S. Pat. No. 4,122,029 may be selected as the emulsifier for its teaching of polydiorganosiloxanepolyoxyalkylene block copolymers containing at least one polydiorganosiloxane block and at least one polyoxyalkylene block.

The silicone polyethers disclosed in U.S. Pat. No. 4,853,474 may be selected as the emulsifier for its teaching of organopolysiloxane-polyoxyalkylene emulsifiers for polar in nonpolar liquid emulsions wherein the organopolysiloxane-polyoxyalkylene polymer molecules are intentionally cross linked through a cross linking agent joined thereto by non-hydrolyzable bonds and being free of internal hydrolyzable bonds.

Silicone polyether elastomers such as those disclosed in U.S. Pat. No. 5,811,487 may be selected as the emulsifier for its teaching of elastomeric silicone polyethers useful as emulsifiers.

The emulsifier may also be a combination or mixture of various emulsifiers, for example any of those described above. The emulsifier may also include the addition of auxillary surfactants. Furthermore, the emulsifier or mixture of emulsifiers may be used neat, or the emulsifier may be dissolved in a hydrophobic solvent, such as a volatile silicone, including the present cyclic siloxanes.

Illustrative, non-limiting commercial products suitable as the emulsifiers include; DC5225C, DC3225C, DC5200, DC9011, DC9040, DC9050 DC8822A, (Dow Corning Corp., Midland, Mich. 48686)

Other additives can also be incorporated in the emulsion, such as fillers, foam control agents; anti-freeze agents and biocides.

In one embodiment, the emulsion contains a buffering agent, such as citric acid.

The cyclic siloxanes, or compositions containing the present cyclic siloxanes such as the aforementioned silicone compositions, can be used in various over-the-counter (OTC) personal care products, medical care, and household care products. Thus, they can be used in antiperspirants, deodorants, skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shower gels, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, color cosmetic removers, and powders. Furthermore, it is anticipated that the cyclic siloxanes cyclic siloxane of the present invention can be combined with various other components to prepare the personal care products. These components include additional surfactants, moisturizers, pigments, sunscreens, fragrances, emollients, commonly used to formulate such personal care products. The cyclic siloxane compositions of the present invention can also be used in sprayable lotions formulations and in various wipe formulations.

EXAMPLES

The following examples are included to demonstrate representative embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C., unless indicated otherwise.

Example 1

Synthesis of Cyclic Siloxane-2,2,4,4,6-pentamethyl-1,3,5-trioxa-2,4-disilacycloheptane

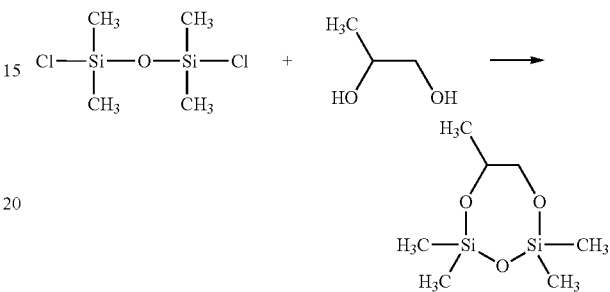

Into a 250-mL, 3-necked flask equipped with magnetic stirrer, addition funnel, condenser, and nitrogen inlet was loaded with ethyl acetate (56.73 g), 1,2-propanediol (8.39 g, 0.110 mol), and pyridine (20.67 g, 0.261 mol). The addition funnel was loaded with dichlorotetramethyldisiloxane (21.18 g, 0.104 mol) and ethyl acetate (39.44 g). The mixture in the addition funnel was added into the reaction stirring at 55° C. under $N_2$ purge. The addition was completed in about 40 minutes. The reaction mixture was held at this temperature for an additional 1 hour and 30 minutes. The resulting mixture was pressure filtered, vacuum stripped to remove volatiles and salts, and then vacuum fraction distilled to yield a clear, low viscosity fluid (6.20 g, 0.0301 mol).

Example 2

Synthesis of Cyclic Siloxane-2,2,4,4,6,6,8-heptamethyl-1,3,5-trioxa-2,4-disilacyclooctane

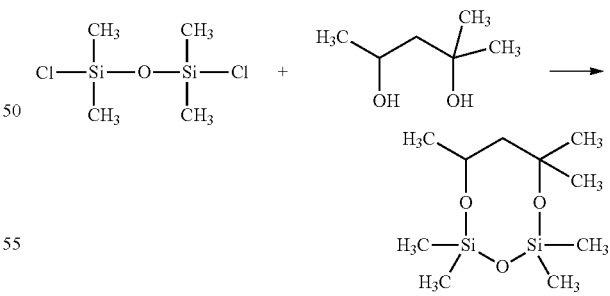

In a 1-L, 3-necked flask equipped with magnetic stirrer, two addition funnels, condenser, and nitrogen inlet was loaded with ethyl acetate (108.56 g) and n-hexylamine (2.02 g). Into addition funnel A was loaded hexylene glycol (47.28 g, 0.400 mol), pyridine (75.33 g, 0.952 mol), and ethyl acetate (57.03 g). Into addition funnel B was loaded dichlorotetramethyldisiloxane (77.61 g, 0.382 mol) and ethyl acetate (53.42 g). The mixtures in funnels A and B were simultaneously added into the reaction stirring at 70° C. under $N_2$ purge. The addition rate was manipulated to allow the glycol and chlorosiloxane to be completely discharged at the same time, after approximately 1 hour. The reaction mixture was held at this temperature an additional 1 hour and 15 minutes. The resulting mixture was pressure filtered, vacuum stripped to remove volatiles and salts, and then vacuum fraction distilled to yield a clear, low viscosity fluid (36.02 g, 0.145 mol).

Example 3

Synthesis of Cyclic Siloxane-2,2,4,4,6,6,8-heptamethyl-1,3,5,7-tetraoxa-2,4,6-trisilacyclodecane

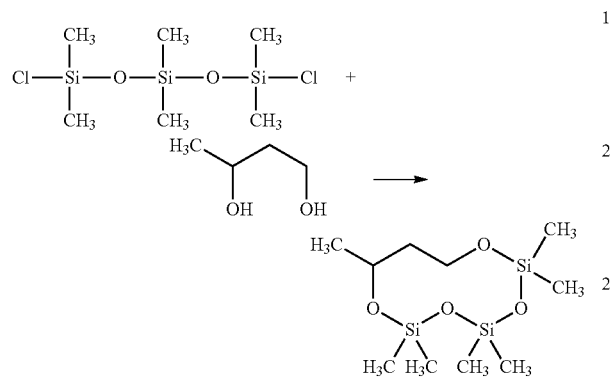

Into a 250-mL, 3-necked round-bottom flask equipped with mechanical stirrer, condenser, nitrogen inlet, KOH bubbler, and two addition funnels was loaded ethyl acetate (50.30 g). Into addition funnel A was loaded 1,3-butanediol (9.32 g, 0.103 mol) and pyridine (23.37 g, 0.295 mol). Into addition funnel B was loaded dichlorohexamethyltrisiloxane (27.31 g, 0.098 mol) and ethyl acetate (13.9 g). The mixtures in funnels A and B were simultaneously added into the reaction flask stirring at 70° C. under $N_2$ purge. The addition rate was manipulated to allow the diol and chlorosiloxane to be completely discharged at the same time, after approximately 1 hour. The reaction was stirred at 70° C. for an additional 2 hours and 30 minutes. The resulting mixture was pressure filtered, vacuum stripped to remove volatiles and salts, and then vacuum fraction distilled to yield a clear, low viscosity fluid (10.57 g, 0.0359 mol).

Example 4

Synthesis of Cyclic Siloxane-2,2,4,4,6-pentamethyl-1,3,5-trioxa-2,4-disilacyclooctane

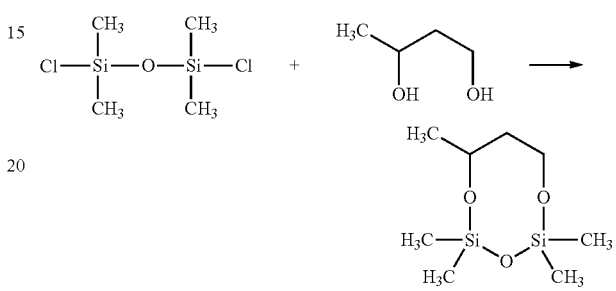

Into a 500-mL, 3-necked flask equipped with magnetic stirrer, addition funnel, condenser, and nitrogen inlet was loaded with ethyl acetate (104.31 g), 1,3-butanediol (19.10 g, 0.212 mol), and pyridine (41.63 g, 0.526 mol). The addition funnel was loaded with dichlorotetramethyldisiloxane (40.93 g, 0.201 mol) and ethyl acetate (60.92 g). The mixture in the addition funnel was added into the reaction stirring at 55° C. under $N_2$ purge. The addition was completed in about 1 hour. The reaction mixture was held at this temperature for an additional 1 hour and 45 minutes. The resulting mixture was pressure filtered, vacuum stripped to remove volatiles and salts, and then vacuum fraction distilled to yield a clear, low viscosity fluid (15.57 g, 0.0707 mol).

Table I summarizes the cyclic siloxanes prepared.

TABLE I

Structure of Cyclic Siloxanes Prepared

| Structure | Alcohol | Product b.p. (° C.) | Surface Tension | Refractive Index |
|---|---|---|---|---|
| (Example 1) | 1,2-Propanediol | 160 | — | — |
| (Example 2) | Hexylene Glycol | 188 | 23.1 | 1.420 |

TABLE I-continued

Structure of Cyclic Siloxanes Prepared

| Structure | Alcohol | Product b.p. (° C.) | Surface Tension | Refractive Index |
|---|---|---|---|---|
| (Example 3) 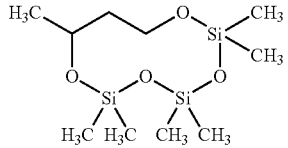 | 1,3-Butanediol | 230 | 21.6 | 1.414 |
| (Example 4) 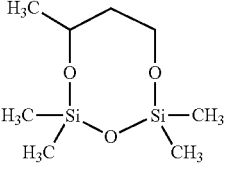 | 1,3-Butanediol | 180 | 22.6 | 1.423 |

Physical Properties

The flash points for Example 2 and Example 3 cyclics were analyzed using the Setaflash closed cup method. Refractive indices were determined by using the Bausch & Lomb Refractometer. An Anton Paar DMA 48 Densimeter was used to measure the densities of the samples. The viscosities were measured using a size #75 Cannon-Manning semi-micro viscometer. Atmospheric boiling points at 739 mmHg were measured using a crude boiling point method, in which boiling points were visually observed by heating 1-ml samples in small Pyrex test tubes. Physical properties of $D_5$, isohexadecane, isododecane, and isodecyl neopentanoate were taken from literature values. The odor of each sample was determined by a panel, which was asked to rate it into one of the four following categories: no smell, faint, mild, and strong. Physical properties of Example 2 and Example 3 along with $D_5$ and some organic solvents are listed in Tables II and III.

TABLE II

Boiling Point, Flashing Point, and Surface Tension of Volatile Cyclic Siloxanes

| Compound | B.P. (° C.) | Flash Point (° C.) | Surface Tension (dynes/cm) |
|---|---|---|---|
| $D_5$ | 210 | 76 | 18.0 |
| Isohexadecane | 230 | 102 | 24.8 |
| Isododecane | 184 | 42 | 22.4 |
| Isodecyl Neopentanoate | 263 | 120 | 26.1 |
| Example 2 | 188 | 64 | 23.1 |
| Example 3 | 230 | 76 | 21.6 |

TABLE III

Refractive Index, Viscosity, Odor, and Density of Volatile Cyclic Siloxanes

| Compound | Refractive Index | Viscosity (cSt) | Odor | Density (g/cm³) |
|---|---|---|---|---|
| $D_5$ | 1.398 | 3.870 | No | 0.959 |
| Isohexadecane | 1.443 | 4.610 | Faint | 0.790 |
| Isododecane | 1.419 | 1.728 | Faint | 0.749 |
| Isodecyl Neopentanoate | 1.428 | 4.522 | Mild | 0.853 |
| Example 2 | 1.420 | 3.171 | Faint | 0.938 |
| Example 3 | 1.414 | 4.657 | Faint | 0.965 |

Volatility

Volatility was studied by placing 0.1 g of sample into an aluminum cup inside a temperature and humidity controlled climatic room (temperature set at 20° C.±1 and humidity set at 50%±5). The volatility was evaluated by taking weight loss measurements at predetermined time intervals for 6 hours.

TABLE IV

Volatility Results at 22° C.

| Time (min) | Example 2 % Wt Remaining | $D_5$ % Wt Remaining |
|---|---|---|
| 35 | 94.39% | 99.25% |
| 95 | 86.68% | 98.03% |
| 160 | 78.26% | 96.57% |
| 227 | 69.78% | 95.12% |
| 293 | 56.57% | 93.68% |
| 360 | 47.02% | 92.24% |

TABLE V

Volatility Results at 37° C.

| Time (min) | Example 2 % Wt Remaining | $D_5$ % Wt Remaining |
|---|---|---|
| 35 | 63.74% | 78.45% |
| 95 | 30.98% | 52.56% |
| 160 | 6.73% | 26.49% |
| 227 | 0.29% | 8.40% |

TABLE V-continued

Volatility Results at 37° C.

| Time (min) | Example 2 % Wt Remaining | $D_5$ % Wt Remaining |
|---|---|---|
| 293 | 0.28% | 0.06% |
| 360 | 0.00% | 0.00% |

Compatibility

Example 2 and Example 3 cyclic siloxanes was found to be compatible with many solvents commonly used in various Life Science applications. Each solvent was tested at three different concentrations at 10%, 50% and 90%. A clear sample (C) indicates that the material is soluble in the solvent in all three solvent loadings. An insoluble sample (I) indicates that the material is insoluble in all three solvent loadings. Example 3 is only partially soluble in castor oil.

TABLE VI

Compatibility with Commonly Used Solvents in Life Science

| | Example 2 | Example 3 | $D_5$ |
|---|---|---|---|
| Isopropyl Myristate | C | C | C |
| Octyl Methoxycinnamate | C | C | C |
| Octyl Salicylate | C | C | C |
| Castor Oil | C | I-C | I |
| Olive Oil | C | C | C |
| Propylene Glycol | I | I | I |
| Glycerin | I | I | I |

TABLE VII

Compatibility with More Commonly Used Solvents in Life Science

| | Example 2 | $D_5$ |
|---|---|---|
| IDD | C | C |
| Caprylic/Capric Triglycerides | C | C |
| Mineral Oil | C | C |
| C12-15 Alkyl Benzoate | C | C |
| Sunflower Oil | C | C |
| Ethanol | C | C |
| Dow Corning ® 200 Fluid, 350 cSt | C | C |

Preparation of Emulsion

To a dental mixer cup was added Example 2 or Example 3 cyclics (29.82 g) and 8.946 g of Dow Corning® 5329 Performance Modifier (a silicone polyether functional emulsifier). The contents of the container were blended via SpeedMixer DAC 150 FVZ for 1 minute. Hostapur SAS-30—a secondary alkane sulfonate—(0.497 g) was added to the resultant mixture and spun on the Speed Mixer for an additional 1 minute. DI $H_2O$ (60.137 g) was premixed with $NaHCO_3$ (0.200 g) and added to the oil/surfactant mixture in 5-g increments followed by 1 minute of mixing until entire quantity of dilution water was added to yield a coarse emulsion. These emulsion particles were then passed through a microfluidizer under conditions favorable to afford particle size 0.1-0.2 um. Upon heat aging the emulsified Example 2 for 4 weeks at 40° C., the emulsion remained homogeneous. Upon heat aging the emulsified Example 3 for 6 weeks at 40° C., the emulsion remained homogeneous.

Emulsion Stability

Example 2 and $D_5$ were both formulated into emulsions with the following ingredients: Dow Corning® 5200 Formulation Aid, citric acid buffer solution, NaCl, and glycerol. Emulsions were heat aged in a 45° C. oven for 1 month or subjected to 5 cycles of the freeze/thaw process (each cycle consisted of holding at −15° C. for 18 hours followed by 25° C. for 6 hours).

TABLE VIII

Emulsion Formulation

| Part A | Parts |
|---|---|
| Dow Corning ® 5200 Formulation Aid | 2% |
| $D_5$ or Example 2 | 20% |
| Part B | |
| Citric Acid Buffer Solution (pH = 6.2) | 71% |
| NaCl | 2% |
| Glycerol | 5% |

Both Example 2 and $D_5$ were intact post extraction from the heat age or freeze/thaw treated emulsions, demonstrating Example 2's similarity to $D_5$ with respect to stability in a standard Life Science formulation.

TABLE IX

Emulsion Heat Aging and Freeze/Thaw Stability

| Volatile Siloxane | Heat Aged at 45° C. (1 month) | Freeze/Thaw (5 cycles) |
|---|---|---|
| $D_5$ | Intact | Intact |
| Example 2 | Intact | Intact |

Silicone Gum Blends

When blended with polydimethylsiloxane gum (Dow Corning SGM-36), Example 2 and Example 3 cyclics demonstrated smaller changes in viscosity relative to solvents such as 3 cSt DC 200 fluid and organic solvents such as IHD. A typical gum blend was prepared by blending 2.01 g of the high molecular weight polydimethylsiloxane (Dow Corning SGM-36) with 8.01 g of Example 2 or Example 3 in a dental mixer until smooth. Viscosity was measured by using a Brookfield cone-plate Rheometer (Model DV-III) at 25° C.

TABLE X

Viscosity of SGM-36 Blended with Volatile Cyclic Siloxanes

| Volatile Solvent | Wt % | Viscosity* |
|---|---|---|
| $D_5$ | 80% | 12,819 |
| 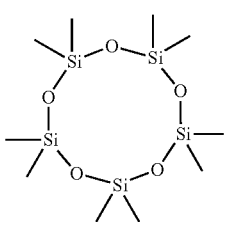 (Example 2) | 80% | 9,162 |
| 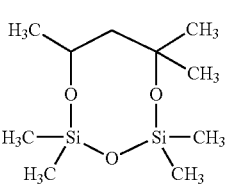 | | |

TABLE X-continued

Viscosity of SGM-36 Blended with Volatile Cyclic Siloxanes

| Volatile Solvent | Wt % | Viscosity* |
|---|---|---|
| (Example 3) | 80% | 13,133 |
| 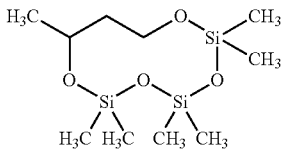 | | |
| (3 cSt) | 80% | 4,435 |
| 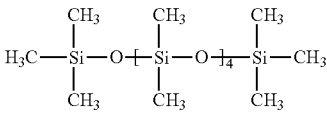 | | |
| Isohexadecane (IHD) | 80% | 4,266 |
| 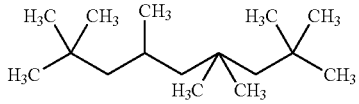 | | |

*A 0.5 g of sample was used to measure the viscosity at 25° C. The Cone-Plate Rheometer had a cone-plate measugin 25 mm in diameter (CP-52) and was typically run at 10-50 RPM to obtain torque reading between 10-90%

Sensory Test Results

Figure 2:
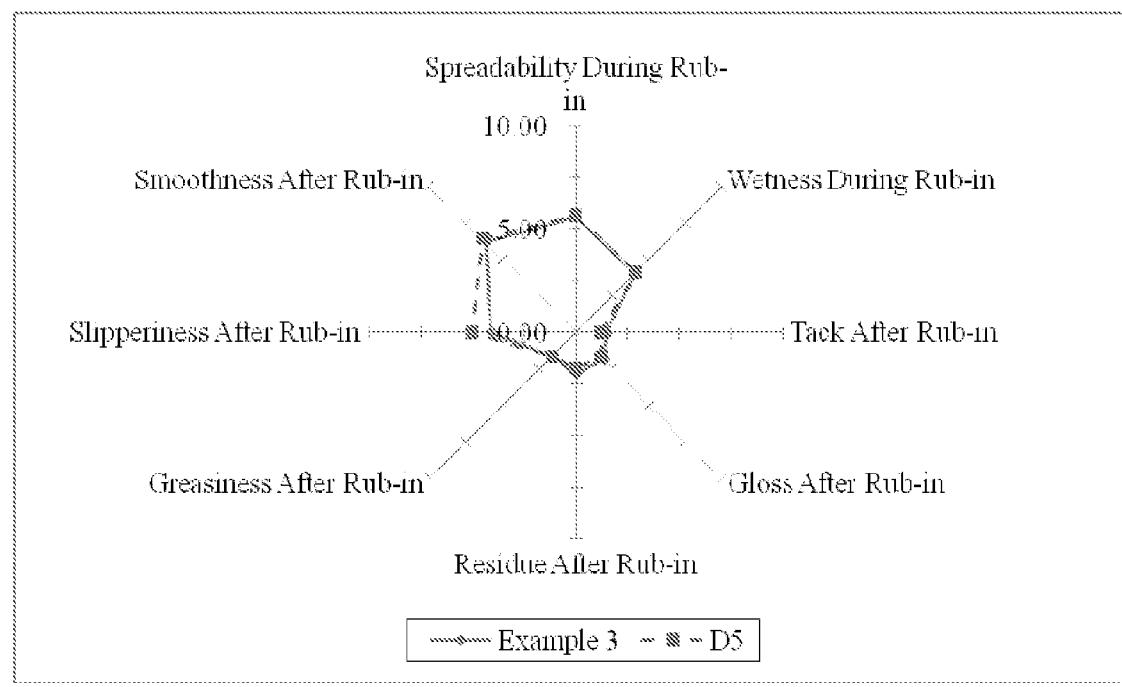
FIG. 2: Sensory Test Results for the Cyclic Siloxane of Example 3 Compared to $D_5$

Several representative cyclic siloxanes were evaluated for their sensory properties using a trained sensory panel. FIGS. 1 and 2 show that Example 2 and Example 3 are very similar to $D_5$ in the sensory properties studied.

The invention claimed is:

1. A cyclic siloxane compound comprising the structural formula

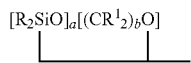

where a≧2 and b≧2,
R is an alkyl group containing 1 to 4 carbon atoms,
$R^1$ is independently hydrogen or methyl,
where the $(CR^1_2)$ segment is
—CH(CH$_3$)CH$_2$CH$_2$— or —CH(CH$_3$)CH$_2$C(CH$_3$)$_2$—.

2. The cyclic siloxane compound of claim 1 where the cyclic siloxane is 2,2,4,4,6,6,8-heptamethyl-1,3,5-trioxa-2,4-disilacyclooctane having the formula;

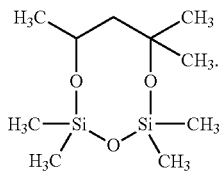

3. The cyclic siloxane compound of claim 1 where the cyclic siloxane is 2,2,4,4,6,6,8-heptamethyl-1,3,5,7-tetraoxa-2,4,6-trisilacyclodecane having the formula;

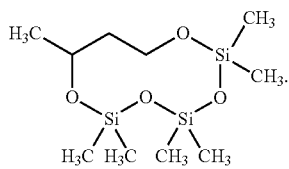

4. The cyclic siloxane compound of claim 1 where the cyclic siloxane is 2,2,4,4,6-pentamethyl-1,3,5-trioxa-2,4-disilacyclooctane having the formula;

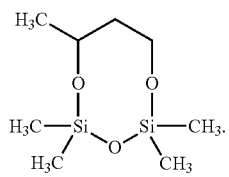

5. A composition comprising the cyclic siloxane according to claim 1 and an additional silicone.

6. The composition of claim 5 where the additional silicone is a silicone gum.

7. An emulsion composition comprising the cyclic siloxane according to claim 1.

8. An emulsion composition comprising the composition according to claim 6.

* * * * *